US010279046B2

(12) United States Patent
Joo et al.

(10) Patent No.: US 10,279,046 B2
(45) Date of Patent: May 7, 2019

(54) EYE DROP COMPOSITION FOR TREATING OCULAR INFLAMMATORY DISEASE AND PREPARATION METHOD THEREFOR

(71) Applicant: CATHOLIC UNIVERSITY INDUSTRY-ACADEMIC COOPERATION FOUNDATION, Seoul (KR)

(72) Inventors: Choun-Ki Joo, Seoul (KR); Jun-Sub Choi, Gyeonggi-do (KR)

(73) Assignee: CATHOLIC UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/774,220

(22) PCT Filed: Mar. 6, 2014

(86) PCT No.: PCT/KR2014/001849
§ 371 (c)(1),
(2) Date: Sep. 10, 2015

(87) PCT Pub. No.: WO2014/142469
PCT Pub. Date: Sep. 18, 2014

(65) Prior Publication Data
US 2016/0193234 A1    Jul. 7, 2016

(30) Foreign Application Priority Data
Mar. 11, 2013 (KR) .................. 10-2013-0025774

(51) Int. Cl.
| | | |
|---|---|---|
| A61K 31/635 | (2006.01) | |
| A61K 47/36 | (2006.01) | |
| A61K 9/00 | (2006.01) | |
| A61K 9/08 | (2006.01) | |
| A61K 47/48 | (2006.01) | |
| A61K 47/10 | (2017.01) | |
| A61K 47/60 | (2017.01) | |

(52) U.S. Cl.
CPC ...... *A61K 47/48215* (2013.01); *A61K 9/0048* (2013.01); *A61K 9/08* (2013.01); *A61K 31/635* (2013.01); *A61K 47/10* (2013.01); *A61K 47/36* (2013.01); *A61K 47/60* (2017.08)

(58) Field of Classification Search
None
See application file for complete search history.

(56) References Cited

U.S. PATENT DOCUMENTS

2008/0286211 A1*  11/2008  Barker ................ A61K 9/0031
                                                  424/45
2010/0040685 A1    2/2010   Lee et al.
2011/0206620 A1    8/2011   Dana et al.

FOREIGN PATENT DOCUMENTS

| CN | 104158901 A | 11/2014 |
|---|---|---|
| JP | 58-037001 | 3/1982 |
| JP | 02-164829 | 6/1990 |
| JP | 1997-169667 A | 6/1997 |
| JP | 11005744 A * | 1/1999 |
| JP | 2005-508866 A | 4/2005 |
| KR | 10-2003-0023098 | 5/2005 |
| KR | 10-0894-0420000 A | 10/2008 |
| KR | 10-2008-0092631 A | 10/2008 |
| KR | 20080092631 A * | 10/2008 |
| KR | 10-2008-0092631 | 4/2009 |
| KR | 10-2009-0053892 | 5/2009 |
| WO | 2013-009519 | 1/2013 |
| WO | WO 2013/006548 | 1/2013 |
| WO | WO 2013/009519 | 1/2013 |

OTHER PUBLICATIONS

Yoshida et al., Clinical evidence of sustained chronic inflammatory reaction in retinitis pigmentosa, Ophthalmology. Jan. 2013;120(1):100-5. doi: 10.1016/j.ophtha.2012.07.006. Epub Sep. 15, 2012, printed from https://www.ncbi.nlm.nih.gov/pubmed/22986109, Abstract only, 2 pages.*
Merck Manuals, Retinitis Pigmentosa, 2005, http://www.merck.com/mmpe/print/sec09/ch106/ch106h.html, printed May 27, 2008, 2 pages.*
Radu et al., Complement system dysregulation and inflammation in the retinal pigment epithelium of a mouse model for Stargardt macular degeneration, J Biol Chem. May 27, 2011;286(21):18593-601. doi: 10.1074/jbc.M110.191866. Epub Apr. 4, 2011, printed from https://www.ncbi.nlm.nih.gov/pubmed/21464132, Abstract only, 2 pages.*
Mayo Clinic, Stargardt's disease: Can it be treated?, 2006, printed May 27, 2008, MayoClinic.com, http://www.mayoclinic.com/print/stargardts-disease/AN00846/METHOD=print, 2 pages.*
Johns Hopkins, Stevens-Johnson Syndrome, https://www.hopkinsmedicine.org, printed from https://www.hopkinsmedicine.org/wilmer/conditions/stevens-johnson.html on Oct. 26, 2016, 2 pages.*

(Continued)

*Primary Examiner* — Gigi G Huang
(74) *Attorney, Agent, or Firm* — Leydig, Voit & Mayer, Ltd.

(57) ABSTRACT

The present invention relates to a composition for treating an ocular inflammatory disease, comprising hydrophilic sulfasalazine and hyaluronic acid, and a preparation method therefor. Furthermore, the present invention relates to a method for treating an ocular inflammatory disease, which comprises administering, to an individual, a therapeutically effective amount of hydrophilic sulfasalazine and hyaluronic acid.

3 Claims, 9 Drawing Sheets

(56) References Cited

OTHER PUBLICATIONS

Cataracts In-Depth Report, The New York Times, Jul. 28, 2009, printed from http://www.nytimes.com/health/guides/disease/cataract/print.html with Google date sheet of public availability, 11 pages.*
Benitez-Del-Castillo et al., (2000), "Sulfasalazine in the prevention of anterior uveitis associated with ankylosing spondylitis", Eye, v14:340-343.
Japanese Office Action for 2015-562904 dated Aug. 28, 2015, 3 pages (in Japanese).
Munoz-Fernandez et al. (2003), "Sulfasalazine Reduces the Number of Flares of Acute Anterior Uveitis Over a One-Year Period", J. Rheumatol, v.30:1277-9.
Translation of Japanese Office Action for application 2015-562904, dated Aug. 15, 2016, 3 pages.
International Search Report for PCT/KR2014/001849 dated Jun. 23, 2014, 4 pages.
Chinese Patent Application No. 201480021005.0, English Translation of Office Action dated Apr. 20, 2017, 23 pages.

* cited by examiner

EYE DROP COMPOSITION FOR TREATING OCULAR INFLAMMATORY DISEASE AND PREPARATION METHOD THEREFOR

RELATED APPLICATIONS

This application is a 35 U.S.C. § 371 national phase application of PCT/KR2014/001849 (WO2014/142469), filed on Mar. 6, 2014 entitled "EYE DROP COMPOSITION FOR TREATING OCULAR INFLAMMATORY DISEASE AND PREPARATION METHOD THEREFOR", which application claims priority to and the benefit of Korean Patent Application No. 10-2013-0025774, filed Mar. 11, 2013, the disclosures of which are incorporated herein by reference in their entirety.

TECHNICAL FIELD

The present invention relates to a composition for treating an ocular inflammatory disease including hydrophilic sulfasalazine and hyaluronic acid and a preparation method therefor. Also, the present invention relates to a method of treating an ocular inflammatory disease comprising administering, to an individual, a therapeutically effective amount of hydrophilic sulfasalazine and hyaluronic acid.

BACKGROUND ART

Eyes are an important receptor receiving much information required for life. The eyes are formed of an inner membrane, a middle membrane, an outer membrane, and a refractive medium, wherein the outer membrane is formed of the cornea or a conjunctiva that is a front surface covering a pupil, and a sclera connected with the cornea or the conjunctiva, the middle membrane is formed of an iris, a ciliary body, and an choroid, and the inner membrane is formed of a retina. A lens, a vitreous body, and an aqueous humor correspond to the refractive medium. The functional disability or loss of the eyes is one of big factors in the degradation of the quality of life. Due to aging, disease, and other factors that negatively affect vision, maintaining the eyes in good health becomes more and more important.

The ocular inflammatory disease refers to a disease related to congestion, swelling, infection, stimulation, or trauma. An anterior segment or an outer (exterior) segment of an eye ball structure includes a front part of an eyeball and proximity tissue and, particularly, has a high possibility of generating an inflammatory disease by being continuously exposed to an environment.

The inflammatory diseases of the anterior and outer segments include corneitis (keratitis), conjunctivitis, keratoconjunctivitis, dry eye syndrome, blepharitis, scleritis, episcleritis, iritis, iridocyclitis, uveitis, or postoperative inflammation. Of these, the keratoconjunctivitis, which is an inflammatory disease generated in a cornea and a conjunctiva due to bacteria, viruses, allergies, or environmental factors, is a general ocular disease, is generally cured well, but in some cases, causes blindness due to tissue damage. As a method of treating the ocular inflammatory diseases, an antihistamine, a steroid such as glucocorticoids, or an allergy preventing and blocking agent is currently being used.

However, although using antibiotics for treating the ocular inflammatory disease is germicidal to infectious bacteria, it is hard to expect effects for inhibiting activation of an inflammatory cell in the cornea and reducing the inflammatory cell. Also, when a steroidal anti-inflammatory drug is used long term or is stopped after long-term use, there are problems in that symptoms, such as general prostration, fever, muscle aches, joint pain and loss of appetite, are generated, the risk of infection caused by bacteria, virus or the like appears, weight is increased and the shape of body is changed, and is often accompanied by insomnia. Particularly, if an ointment or eye drops of glucocorticoids is used long term by patient's arbitrary decision, side effects, such as glaucoma, cataracts or bacterial infection easily occur due to an increase in intraocular pressure.

Hereupon, there have been many advances in technique related to treatment and prevention for an ocular inflammatory disease over the past few years. However, an improved method and composition for preventing and treating an ocular inflammatory disease are still required.

In the present invention, to solve a problem of degradative damage recovery of corneal epithelial cells, which is a problem of antibiotics or steroidal anti-inflammatory eye drops used to treat an ocular inflammatory disease, sulfasalazine-hyaluronic acid mixture eye drops are developed as a medicine for damage recovery of corneal epithelium instrumental in cytothesis.

In this regard, Korean Patent No. 0490286 discloses an eye drop composition for treating retina damage, using sulfasalazine or a soluble salt thereof as an active ingredient, capable of treating ischemia of a retina due to glaucoma, retinal damage due to diabetic retinopathy, atrophy of a retina nerve due to uveitis and the like.

Also, Korean Patent No. 0894042 discloses the composition capable of reducing after-cataract by using a sulfasalazine-hyaluronic acid mixture.

However, there is no known technique to apply a hydrophilic sulfasalazine and hyaluronic acid complex in treatment for an ocular inflammatory disease, in particular an inflammatory disease of anterior and outer segments anywhere in the prior literature, including the above patent documents.

DISCLOSURE

Technical Problem

The present inventors has completed the present invention by confirming effects of hydrophilic sulfasalazine and hyaluronic acid complex eye drops to reduce inflammation and corneal edema and treat dry eye using a corneal inflamed animal model.

Technical Solution

One aspect of the present invention provides an eye drop composition for treating an ocular inflammatory disease comprising hydrophilic sulfasalazine and hyaluronic acid.

Also, the present invention provides a method of treating an ocular inflammatory disease comprising administering, to an individual, a therapeutically effective amount of hydrophilic sulfasalazine and hyaluronic acid.

Another aspect of the present invention provides a preparation method for the eye drop composition for treating an ocular inflammatory disease comprising hydrophilic sulfasalazine and hyaluronic acid.

Advantageous Effects

The sulfasalazine-hyaluronic acid complex eye drops of the present invention, which is a medicine for treating an ocular inflammatory disease, are safely used as a nonsteroidal medicine to reduce side effects caused by conventional antibiotics or a steroidal drug-based medicine.

MODES OF THE INVENTION

Figure 1:
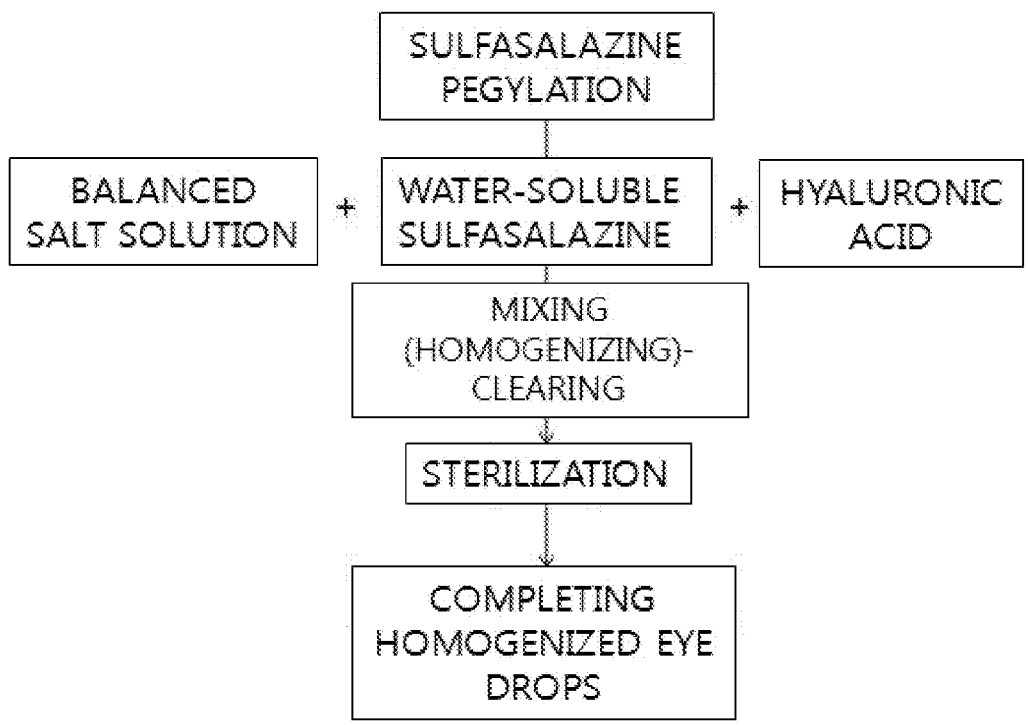
FIG. 1 is a diagram illustrating a preparation process of hydrophilic sulfasalazine-hyaluronic acid complex eye drops.

As one aspect, the present invention relates to an eye drop composition for treating an ocular inflammatory disease comprising hydrophilic sulfasalazine and hyaluronic acid.

As another aspect, the present invention relates to a method of treating an ocular inflammatory disease comprising administering, to an individual, a therapeutically effective amount of hydrophilic sulfasalazine and hyaluronic acid.

In the present invention, sulfasalazine is a compound formed by azo-bonding sulfapyridine and 5-aminosalicylic acid (5-ASA).

The sulfasalazine is poorly water-soluble in an aqueous solution, and so, to be used as a drug, the sulfasalazine needs to be solubilized into hydrophilic sulfasalazine. The hydrophilic sulfasalazine may be obtained in a form of an acid addition salt or alkali addition salt by adding hydrochloric acid, sodium chloride, or potassium chloride to sulfasalazine and, more preferably, may be obtained by performing PEGylation on sulfasalazine.

Preferably, the hydrophilic sulfasalazine of the present invention may include a pegylated sulfasalazine. The pegylated sulfasalazine may be obtained by adding sulfasalazine to a balanced salt solution comprising polyethylene glycol. The balanced salt solution may comprise polyethylene glycols at various molecular weights and concentrations and, for example, may include polyethylene glycol with a weight-average molecular weight of 300 to 500, or, preferably, 380 to 420 at a concentration of 0.1 to 5% (v/v), or preferably, 1% (v/v) or more.

In the present invention, the concentration of the hydrophilic sulfasalazine may be 0.005 to 0.1% (w/v) or, preferably, 0.01 to 0.05% (w/v). If less than the concentration range, an operative medicinal effect for treating keratoconjunctivitis sicca may be poorly achieved. If greater than the concentration range, toxicity for corneal epithelial cells may occur.

In the present invention, the hyaluronic acid is a main component of extracellular matrix, which is known to mechanically protect a tissue, such as a retina or an iris, vascular endothelial cells, epithelial cells and the like and function as a buffer by being widely distributed in extracellular matrix in a connective tissue and forming an adhesive elastic solution under a physiological condition.

In the present invention, the properties, shape, or size of hyaluronic acid is not limited, and is preferably aseptically processed. More preferably, hyaluronic acid with a weight-average molecular weight of $1.0 \times 10^6$ to $4.0 \times 10^6$ g/mol may be used.

Also, the hyaluronic acid may be used in a form of a pharmaceutically acceptable salt, wherein the pharmaceutically acceptable salt includes a sodium salt, potassium salt, calcium salt and the like, and preferably includes the sodium salt.

Preferably, in the present invention, the concentration of hyaluronic acid is 0.01 to 0.5% (w/v), more preferably, 0.05 to 0.2% (w/v). If less than this range, there is a problem in that viscoelasticity is too low to have adequate dampness and lubrication. If greater than this range, excessively high viscoelasticity causes inadequate permeability, and thus there is a problem of being difficult to ensure the liquidity appropriate as eye drops.

The present inventors have provided a composition capable of reducing after-cataract using a sulfasalazine-hyaluronic acid mixture. In the prior art, in the case of an operation on after-cataract, the volume in eyeballs has to be maintained by injecting a sulfasalazine-hyaluronic acid mixture, and thus it is necessary to prepare a high viscoelastic composition comprising the hyaluronic acid in a high concentration of 2.0% (w/v).

On the contrary, in the present invention, it is newly discovered that the sulfasalazine-hyaluronic acid mixture is effective for treatment of an ocular inflammatory disease. The sulfasalazine-hyaluronic acid mixture is formulated as a composition in which hyaluronic acid completely dissolves by lowering the concentration of hyaluronic acid to 0.01 to 0.5% (w/v) to be provided as an eye drop composition for treating an ocular inflammatory disease.

In the present invention, the hydrophilic sulfasalazine and hyaluronic acid mixture may be used to treat, improve, and/or alleviate an ocular inflammatory disease.

The eye drop composition of the present invention may further comprise pharmaceutically acceptable additives. The pharmaceutically acceptable additive is a carrier or diluent that does not remarkably stimulate an organism and hinder biological activity and properties of an administered active ingredient. An example of the pharmaceutically acceptable additive is an isotonic agent, a buffering agent, a stabilizer, a pH adjusting agent and the like.

The eye drop composition according to the present invention is desirably a liquid medicine, so may further comprise a carrier including an aqueous solution.

The carrier including an aqueous solution may include one or more pharmaceutically acceptable carriers selected from the group consisting of distilled water, phosphate buffered saline, a balanced salt solution, and saline. The content of the used carrier may be adjusted according to the amount required for the total capacity of an eye drop to be prepared.

Also, the eye drops of the present invention may further comprise a pharmaceutically acceptable salt. An example of the pharmaceutically acceptable salt may be hydrochloric acid, sodium chloride, potassium chloride, and a mixture thereof.

The term "administrating" in the present invention means that a component of the present invention is introduced to a patient in an appropriate method. The administration route of the present invention means topical administration to an eyeball. In the present specification, a term "treating" means stopping, delaying, or improving the progress of a disease when used for an object showing symptoms of a disease. A method for treating an ocular inflammatory disease of the present invention comprises administering a therapeutically effective amount of hydrophilic sulfasalazine and hyaluronic acid. Those skilled in the art will appreciate that the appropriate daily therapeutic dose may be determined in a correct medical decision by a doctor. The therapeutically effective amount for a specific patient is applied differently depending on the type and degree of reaction to be achieved, the age, weight, general physical condition, sex, and diet of patient, administration time, treatment period, various factors including a drug to be used with, and similar factors well-known in the pharmaceutical sector.

The ocular inflammatory disease of the present invention may include all inflammatory diseases related to an eyeball. The inflammation may refer to symptoms related to congestion, swelling, infection, stimulation, or trauma.

As an example, the ocular inflammatory disease of the present invention may include inflammatory diseases of an anterior segment and an outer segment.

For example, the inflammatory diseases of an anterior segment and an outer segment may include corneitis, conjunctivitis, keratoconjunctivitis, dry eye syndrome, blepharitis, scleritis, episcleritis, iritis, iridocyclitis, uveitis, or a postoperative inflammation.

As another example, the ocular inflammatory disease of the present invention may include an inflammatory disease related to a cornea, conjunctiva or keratoconjunctivitis. There may be mentioned the following diseases, for example:

1) inflammatory disease related to dry eye: keratoconjunctivitis sicca or an ocular inflammation related thereto, ocular inflammation caused by a lack of tears of a patient in which generation of tears is inhibited, or a keratoconjunctivitis epithelial injury related to dry eye syndrome 2) non-infectious keratoconjunctivitis: keratoconjunctivitis generated by an external damage (for example, the case of directly damaging a cornea, the case of damage due to acid or salt, the case of damage due to a burn, or the case of wearing a contact lens), allergic keratoconjunctivitis (for example, hyperpyrexial fever keratoconjunctivitis, vernal keratoconjunctivitis, atopic keratoconjunctivitis, phlyctenular keratoconjunctivitis, keratoconjunctivitis due to contagious blepharitis and the like), acute or chronic non-infectious keratoconjunctivitis with hyperemia accompanying serious edema and angiopathy, non-infectious inflammatory disease of the anterior segment (for example, former uveitis, episcleritis, and scleritis) or keratoconjunctivitis after an ophthalmic operation (for example, strabismus incision surgery, and cataract or glaucoma surgery)

3) infectious keratoconjunctivitis: viral keratoconjunctivitis, bacterial keratoconjunctivitis, fungal keratoconjunctivitis, chlamydial keratoconjunctivitis, rikechia keratoconjunctivitis, or parasitic keratoconjunctivitis As another aspect, the present invention relates to a preparation method for an eye drop composition for treating keratoconjunctivitis comprising hydrophilic sulfasalazine and hyaluronic.

As a preferable aspect, the present invention relates to the preparation method for an eye drop composition for treating keratoconjunctivitis comprising:

(a) a step of hydrophilizing sulfasalazine; and (b) a step of adding hyaluronic acid to the hydrophilized sulfasalazine and mixing hyaluronic acid with the hydrophilized sulfasalazine.

The step (a) is a step of hydrophilizing a sulfasalazine. The known methods and apparatus to be generally used to solubilize poorly soluble compounds may be used without limitation. Preferably, the step (a) may include a step of PEGylating the sulfasalazine.

Specifically, the step of pegylating the sulfasalazine may include a step of adding the sulfasalazine to a balanced salt solution including polyethylene glycol. The polyethylene glycol included in the balanced salt solution may be hydrophilized by pegylating the sulfasalazine. Therefore, when the sulfasalazine is pegylated and hydrophilized, the sulfasalazine may be used as a soluble liquid without changing a chemical structure, and may be easily produced into eye drops. The specific details relating to the sulfasalazine and polyethylene glycol are as follows.

Preferably, the step (a) may include a step of adjusting the concentration of the hydrophilized sulfasalazine to be 0.005 to 0.1% (w/v).

The step (b) is a step of adding and mixing hyaluronic acid with the hydrophilized sulfasalazine. The concentration may be adjusted by adding an appropriate amount of hyaluronic acid to a balanced salt solution including hydrophilized sulfasalazine. The physical properties, form, size and the like of hyaluronic acid, are not limited, and the hyaluronic acid is preferably aseptically processed.

Preferably, the step (b) may include a step of adjusting the concentration of hyaluronic acid to be 0.01 to 0.5% (w/v).

In the step of mixing the hyaluronic acid with the hydrophilized sulfasalazine, it is preferable that the hydrophilized sulfasalazine and hyaluronic acid are mixed for 6 to 24 hours at 20 to 35° C. If less than the temperature range at the time of mixing, the components of eye drops may not be uniformly mixed. If greater than the temperature range, since preparing stable formulation is not easily performed, it is not preferable. Also, if less than the range of mixing time, components of eye drops may not be uniformly mixed. If greater than the time, the viscosity of hyaluronic acid may be changed.

Meanwhile, the method of preparing an eye drop composition for treating keratoconjunctivitis may further include a step of adding pharmaceutically acceptable additives, a carrier, or a salt. The pharmaceutically acceptable carrier or salt may be added in a process of preparing an eye drop composition for treating keratoconjunctivitis without any restriction, but may be preferably added after the hydrophilized sulfasalazine and the hyaluronic acid are completely mixed.

Hereinafter, exemplary embodiments of the present invention will be described in detail. The below exemplary embodiments exemplifies the present invention, but the present invention is not limited to the exemplary embodiments disclosed below.

EXAMPLE 1

Preparation of Sulfasalazine-hyaluronic Acid Complex Eye Drops

Sulfasalazine (Sigma Aldrich Co.) was added to 10 ml of a balanced salt solution (pH 7.4) mixed with polyethylene glycol 30% (w/v) (molecular weight 400, Sigma Aldrich Co.) at a concentration of 5 mg/ml and was mixed by a stirrer for six hours to be PEGylated and solubilized, and thus the solubilized sulfasalazine was prepared.

Then, hyaluronic acid powders (Sigma Aldrich Co.) was mixed in 10 ml of balanced salt solutions at 0.1% (w/v). The solution including the pegylated sulfasalazine was mixed with the hyaluronic acid so that the sulfasalazine is at a concentration of 0.05% (0.5 mg/ml). The concentration of sulfasalazine was adjusted in the PEGylation step. All solutions were stirred at room temperature for six hours to be homogenized. When the solutions became transparent and clear, the solutions were used as eye drops (FIG. 1).

EXAMPLE 2

Confirming Toxicity on a Corneal Epithelial Cells According to Concentration of Sulfasalazine-hyaluronic Acid Complex Eye Drops To observe cytotoxicity on corneal epithelial cells, the human corneal epithelial cell line (HCET) was cultured. The cytotoxicity on the incubated cells was confirmed using a CCK assay (Cell Counting Kit-8, Dojindo molecular technologies, INC).

More specifically, the corneal epithelial cells used in the present invention are the HCET cells which are made by infecting with Simian Virus 40. The cells were distributed from Prof. Kaoru Araki-Sasaki of the School of Medicine, Osaka University, Japan. The corneal epithelial cells were incubated in a thermo-hygrostat at 37° C. in which 5% $CO_2$ is maintained using a cell culture medium (MEM:Ham F12=1:1) added with 5% fetal bovine serum (FBS), 5 mg/mL insulin, 0.1 mg/mL cholera toxin, 10 ng/mL human epidermal growth factor (hEGF), and 0.5% dimethyl sulfoxide (DMSO). In the example, the corneal epithelial cells (HCET) was cultured on a 6-well plate at $2 \times 10^4$ (cells/well) per well.

Then, 24 hours after the culture of the HCET cells under the above condition, the sulfasalazine-hyaluronic acid complex eye drops were treated in a serum-free cell culture medium at the ratio of cell culture medium to eye drops of 5:1 by changing only the concentration of sulfasalazine (0.005 to 5.0 mg/ml). The control group was the serum-free cell culture medium. Then, 12 hours after the drug treatment, the cytotoxicity was confirmed using the CCK assay.

Figure 2:
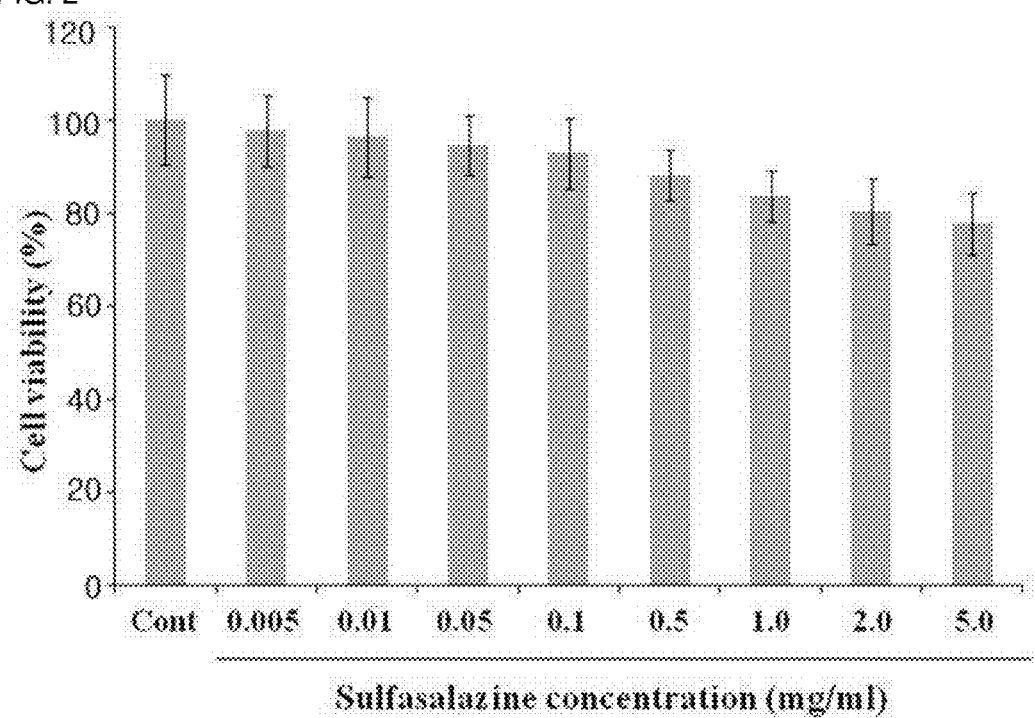
FIG. 2 is a graph illustrating cytotoxicity of a hyaluronic acid complex with respect to concentration of sulfasalazine for corneal epithelial cells.

As a result, the sulfasalazine hyaluronic acid complex eye drops showed a cell viability of 70% or more when the concentration of sulfasalazine is increased up to 5 mg/ml (0.5%, w/v) (FIG. 2).

EXAMPLE 3

Effect of Reducing Keratoconjunctivitis of Sulfasalazine-hyaluronic Acid Complex Eye Drops A white mouse (Sprague Dawley, 300 g, male) was used as an animal, and a corneal damage model (alkali burn) due to a chemical drug using NaOH was used. A paper disk of 3 mm was dipped in a 0.1 N NaOH solution (50 ul), and the cornea was covered with the paper disk for 30 seconds to induce the cornea to be damaged. The inflammation reaction in the cornea was confirmed by performing hematoxylin eosin staining and immunostaining on the F4/80 antigen. The analysis of corneal edema was performed using a ratio of corneal epithelium and corneal stroma.

After the damage to the cornea, the solubilized sulfasalazine and the sulfasalazine-hyaluronic acid eye drop prepared in the Example 1 were administered twice a day, respectively. 0.1% hyaluronic acid was administered to the control group.

Figure 3:
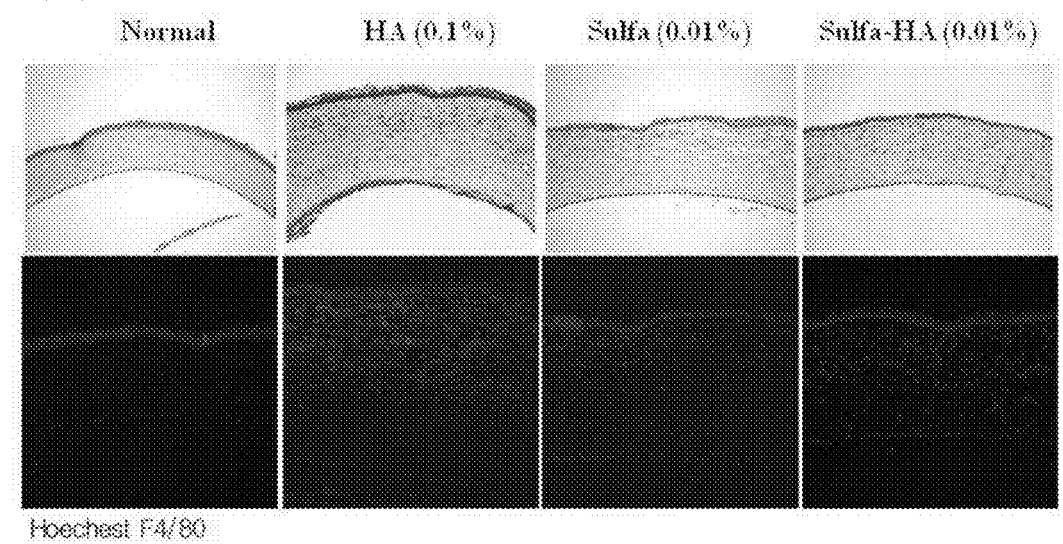
FIG. 3 is a tissue photograph captured after administering, to a corneal inflamed animal model, hyaluronic acid (HA 0.1%), solubilized sulfasalazine (0.01%), or a solubilized sulfasalazine-hyaluronic acid complex (Sulfa-HA 0.01%) respectively, and a tissue staining photograph for an antigen F4/80, which is a macrophage marker.

Three days after the damage to the cornea, the eyeball was removed and a paraffin block was prepared to make a tissue slice, and the hematoxylineosin staining and the immunostaining on the F4/80 antigen as a macrophage marker were performed. As a result, edema of the cornea and the penetration of inflammatory cells into the cornea were observed in the control group. The edema and the number of inflammatory cells were reduced in the group into which the sulfasalazine-hyaluronic acid complex eye drops were administered. Also, the sulfasalazine-hyaluronic acid complex eye drops were more effective in reducing inflammation and edema than a sulfasalazine solution not mixed with hyaluronic acid at the same concentration (FIG. 3).

Figure 4:
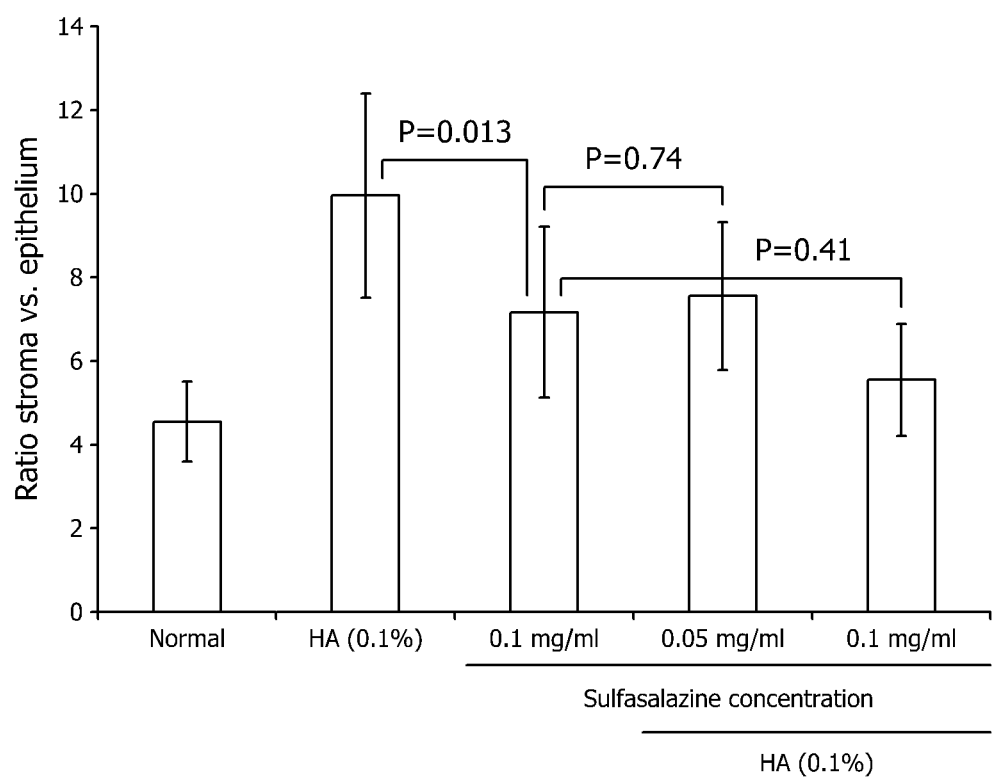
FIG. 4 is a graph illustrating an effect of treatment for corneal edema after administrating, to a corneal inflamed animal model, hyaluronic acid (HA 0.1%), a solubilized sulfasalazine (0.1 mg/ml), or solubilized sulfasalazine (0.1 mg/ml or 0.05 mg/ml)-hyaluronic acid mixture, respectively.

The quantitative result showed that the ratio of normal corneal epithelium and stroma was 4.6±1, and was increased to 10±2.5 after the inducement of cornea inflammation. In the case of the experimental group into which the sulfasalazine-hyaluronic acid complex eye drops are administrated, the group administrated with 0.05 mg/ml sulfasalazine-hyaluronic acid complex eye drops (0.005%) was 7.6±1.8, and a group injected with 0.1 mg/ml (0.01%) was 5.6±1.4, and thus it was confirmed that corneal edema is reduced. Also, an experimental group into which a 0.1 mg/ml sulfasalazine solution (0.01%) was administered was at 7.1±2.1. As a result, the sulfasalazine-hyaluronic acid complex eye drops were more excellent in an effect of reducing corneal edema than the sulfasalazine solution not mixed with hyaluronic acid at the same concentration (FIG. 4).

Figure 5:
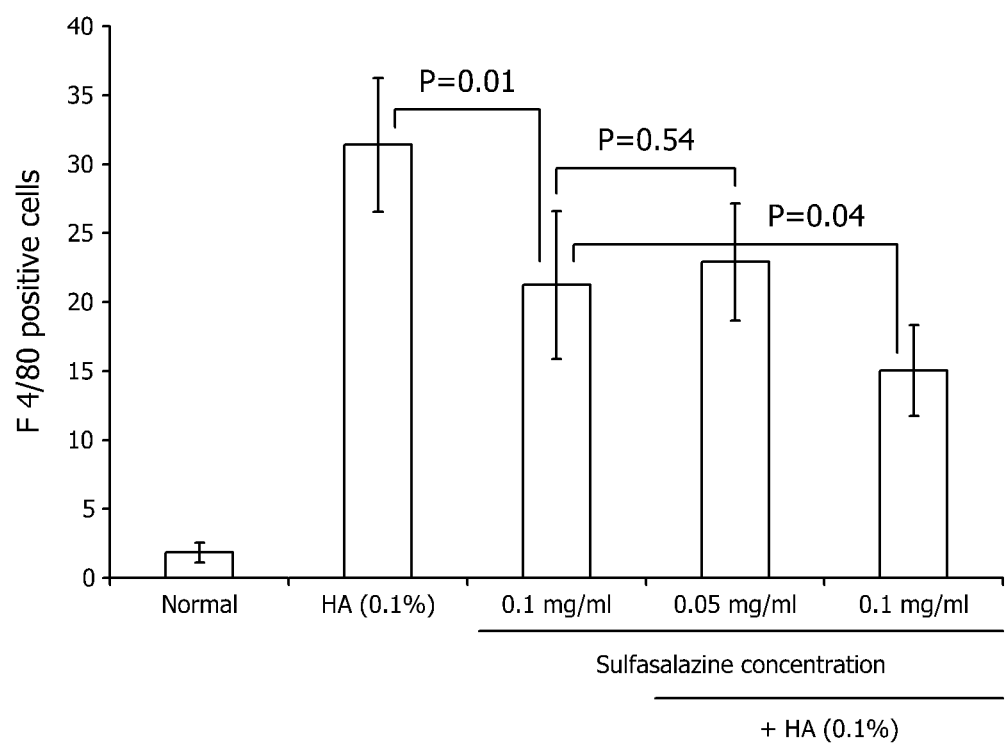
FIG. 5 is a graph illustrating an effect of reducing corneal inflammatory cells after administering, to a corneal inflamed animal model, hyaluronic acid (HA 0.1%), a solubilized sulfasalazine (0.1 mg/ml), or a solubilized sulfasalazine (0.1 mg/ml or 0.05 mg/ml) hyaluronic acid mixture, respectively.

The analysis on the inflammatory cells was performed with respect to the number of macrophages (F4/80 positive cells) present in the cornea. As a result, the number of macrophages was 31.5±4.9 after the inducement of cornea inflammation. The number of macrophages was 21.3±5.5 in a group administered with a sulfasalazine solution without 0.1 mg/ml hyaluronic acid (0.01%), and the number of macrophages was 16.2±3.3 in a group administered with 0.1 mg/ml sulfasalazine-hyaluronic acid complex eye drops (0.01%) (FIG. 5).

EXAMPLE 4

Effect of Reducing Inflammation in Keratoconjunctivitis Sicca of Sulfasalazine-hyaluronic Acid Complex Eye Drops For a test for keratoconjunctivitis sicca, an animal model with dry eye was prepared, and a white mouse (sd rat) was used as an animal. The inducement of the keratoconjunctivitis sicca was performed by applying eyewash with 1% atropine sulfate and 0.1% benzalkonium chloride twice a day for two weeks.

A sulfasalazine-hyaluronic acid complex (0.1 mg/ml) was eyewash-administered twice a day for a week from a week after the administration of 1% atropine sulfate and 0.1% benzalkonium chloride. 0.1% hyaluronic acid and 0.05% cyclosporine eye drops were used as comparative drugs.

Figure 6:
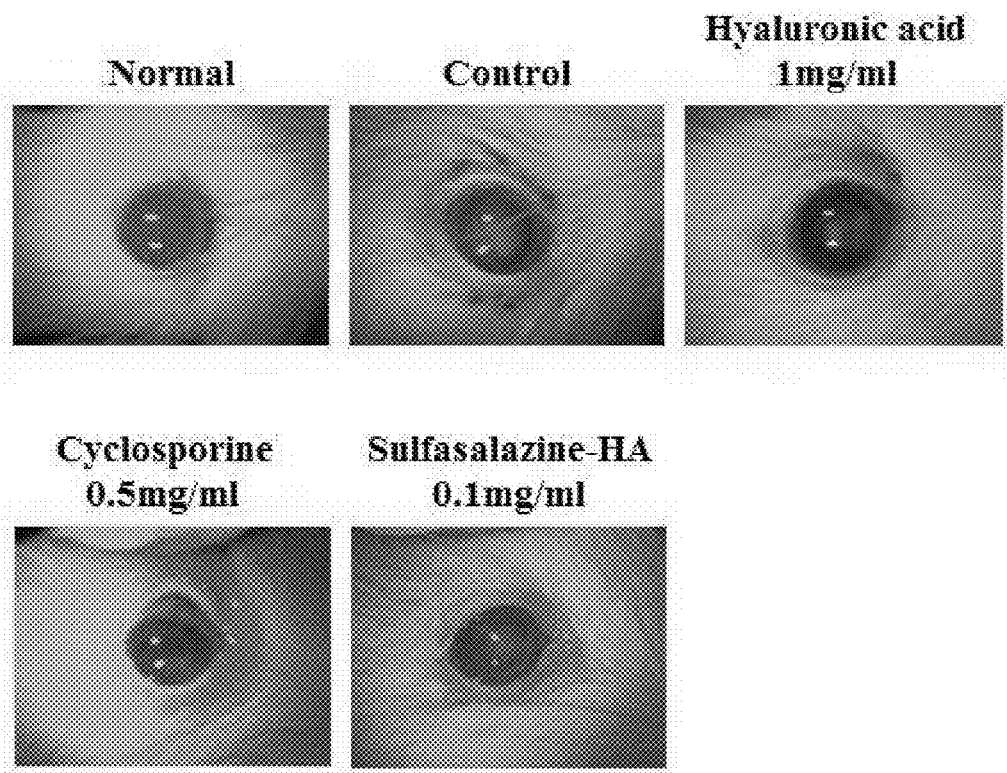
FIG. 6 is a photograph of a damaged area of a cornea (area stained in yellow) stained with 2% fluorescein dye after administering hyaluronic acid (HA 0.1%), cyclosporine 0.05%, a solubilized sulfasalazine-hyaluronic acid complex (Sulfa-HA 0.01%) to animal models with keratoconjunctivitis sicca, respectively.

The confirmation of damage to corneal epithelium in the animal model with keratoconjunctivitis sicca was performed by staining a damaged portion of a corneal epithelium with a 2% fluorescein solution (FIG. 6). The inflammation of the cornea was confirmed by performing cryosectioning on the cornea and staining the cornea with hematoxylin and eosin (FIG. 8).

Figure 7:
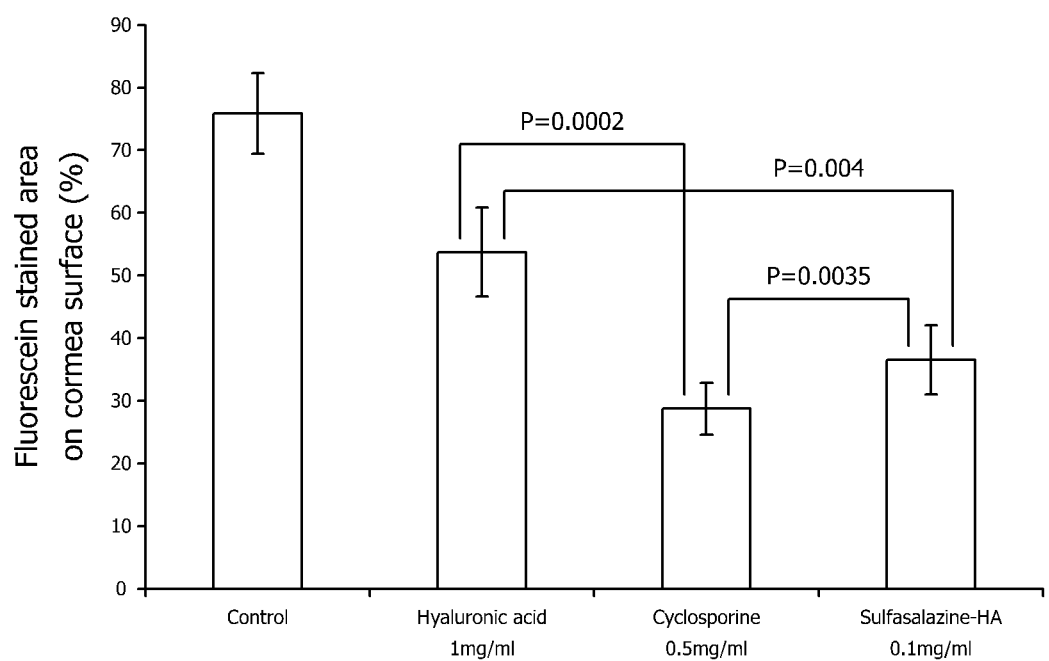
FIG. 7 is a graph illustrating a quantified effect of a drug for corneal damage after administering hyaluronic acid (HA 0.1%), cyclosporine 0.05%, a solubilized sulfasalazine-hyaluronic acid complex (Sulfa-HA 0.01%) to animal models with keratoconjunctivitis sicca, respectively.

In the cornea in which the keratoconjunctivitis sicca (dry eye) is induced, damage to the corneal epithelium due to dry eye was confirmed by staining the corneal epithelial cells with fluorescein (FIG. 6). Normal corneal epithelial cells are not stained with the fluorescein dyen, and only a damaged portion or a portion of the cornea in which the corneal epithelium is not present is stained (area stained in yellow). After staining with the fluorescein dye, the ratio of the stained area to the entire cornea area was represented as a percentage (%). Most of the corneal surface in a control group (non-drug treatment group) was stained, and the ratio of the stained area to the entire cornea area was 76±6.5%. A group with the hyaluronic acid (0.1%) was 54±7.4%, and a group with the cyclosporine (0.05%) was 29±4.2%. A group with the sulfasalazine-hyaluronic acid complex (0.01%) was 37±5.7%, and thus it was observed that the fluorescence staining on the cornea surface was remarkably decreased (FIGS. 6 and 7). Therefore, it was observed that the sulfasalazine-hyaluronic acid complex (0.01%) is effective in reducing damage to corneal epithelial cells and protecting corneal epithelial cells.

Figure 8:
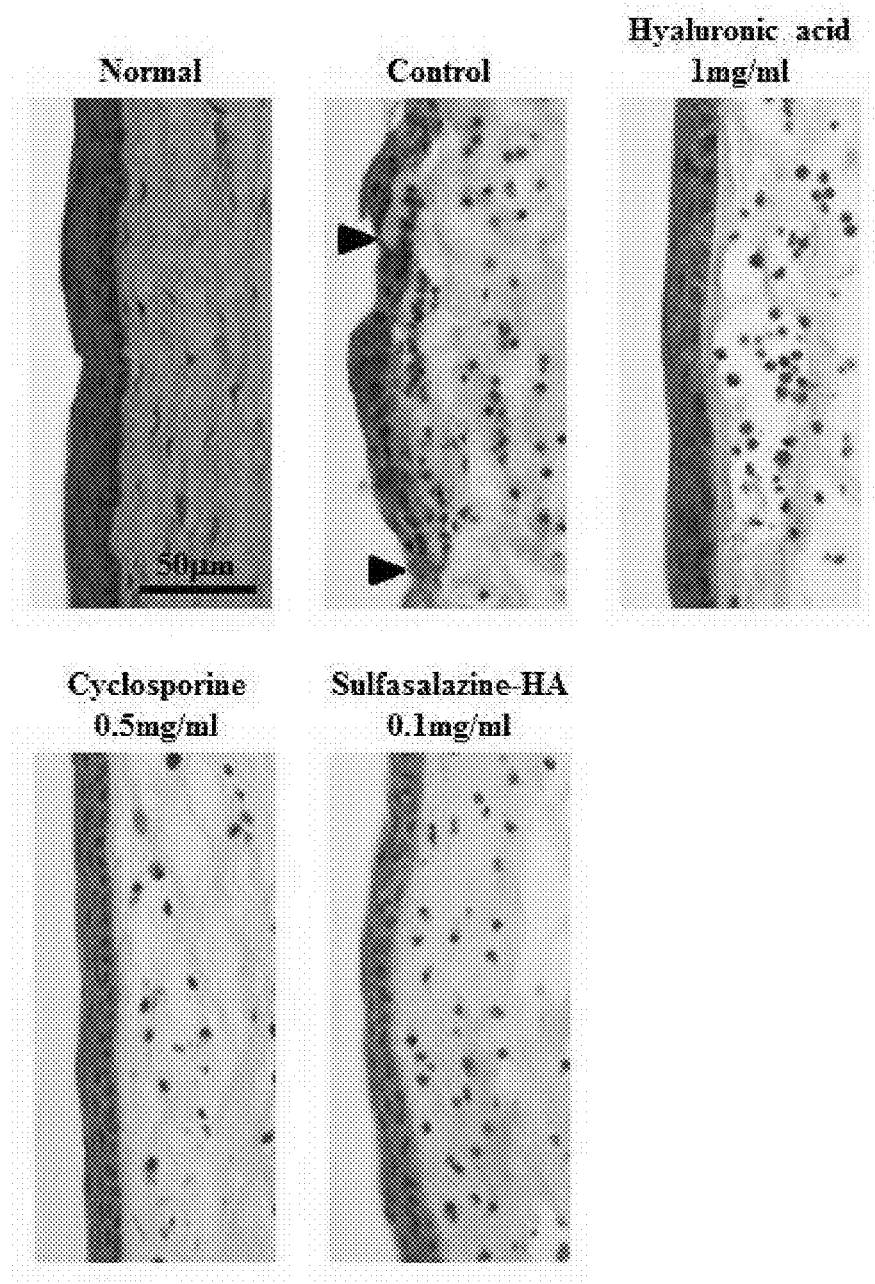
FIG. 8 is a photograph of a cornea cryosectioned and stained with a hematoxylin-eosin to observe inflammatory cells in the cornea after administering hyaluronic acid (HA 0.1%), cyclosporine 0.05%, a solubilized sulfasalazine-hyaluronic acid complex (Sulfa-HA 0.01%) to animal models with keratoconjunctivitis sicca, respectively.
Figure 9:
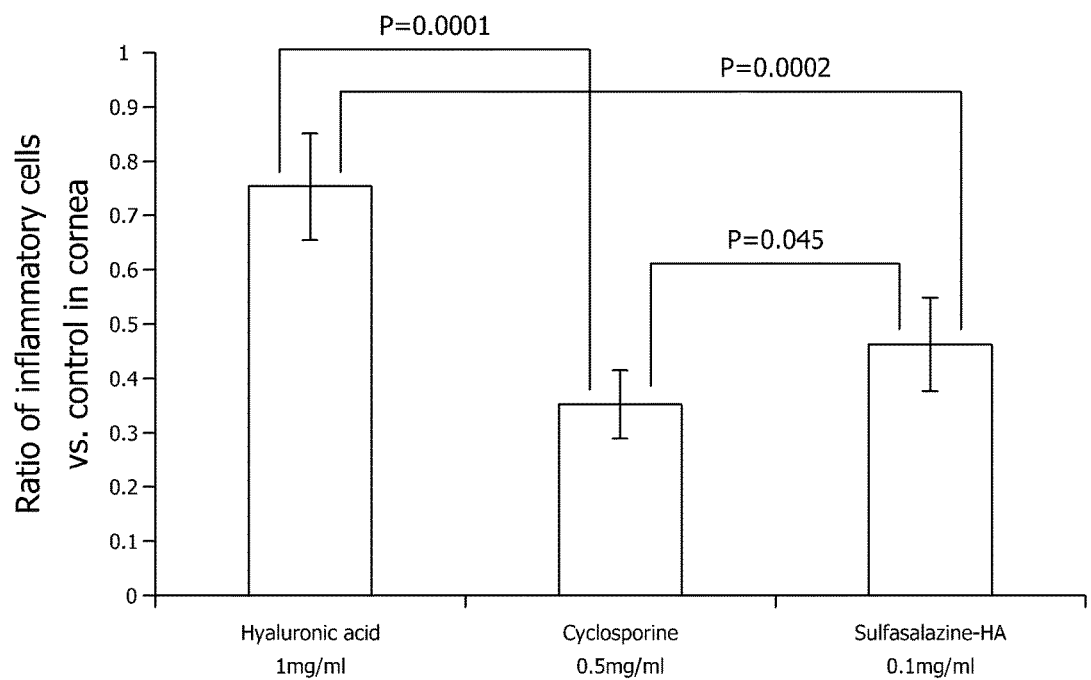
FIG. 9 is a graph illustrating a quantified effect of a drug for corneal damage after administering hyaluronic acid (HA 0.1%), cyclosporine 0.05%, a solubilized sulfasalazine-hyaluronic acid mixture (Sulfa-HA 0.01%) to animal models with keratoconjunctivitis sicca, respectively.

As a result of hematoxylin-eosin staining to confirm an inflammatory cell in the cornea with the keratoconjunctivitis sicca (dry eye), spherical polynucleocytes with polynuclei were observed in the cornea of the dry eye (FIG. 8). In the keratoconjunctivitis sicca model, an effect of suppressing corneal penetration of inflammatory cells was shown as a ratio of each experimental group to the control group (non-drug treatment group). The inflammation-reducing effect was 0.76±0.1 in the hyaluronic acid (0.1%) group, 0.35±0.07 in the cyclosporine (0.05%) group, and 0.48±0.09 in the sulfasalazine-hyaluronic acid complex (0.01%) group (FIG. 9). As a result of the animal test, it was confirmed that the sulfasalazine-hyaluronic acid complex (0.01%) was effective in suppressing inflammation of keratoconjunctivitis sicca.

The result of the examples show that the sulfasalazine-hyaluronic acid complex eye drops are effective in alleviating cornea inflammation, and are more effective than administrating sulfasalazine alone.

According to the result, the sulfasalazine-hyaluronic acid complex eye drops of the present invention can be used effectively for treatment of inflammation of eyeball, in particular, an anterior or outer segment.

The invention claimed is:

1. A method of treating keratoconjunctivitis, the method consisting of:
   administering, to an individual, a therapeutically effective amount of an eye drop composition consisting of hydrophilic sulfasalazine, hyaluronic acid, and excipients, wherein the hydrophilic sulfasalazine is a PEGylated form of sulfasalazine, and wherein the composition is effective to treat the inflammation.

2. The method of claim 1, wherein a concentration of the hydrophilic sulfasalazine is 0.005 to 0.1%(w/v).

3. The method of claim 1, wherein a concentration of the hyaluronic acid is 0.01 to 0.5%(w/v).

* * * * *